United States Patent
Mahmoud

(10) Patent No.: US 10,034,622 B1
(45) Date of Patent: Jul. 31, 2018

(54) IN-SHOE FOOT MONITORING UTILIZING AN INSERT

(71) Applicant: Fadi A. Mahmoud, Sausalito, CA (US)

(72) Inventor: Fadi A. Mahmoud, Sausalito, CA (US)

( * ) Notice: Subject to any disclaimer, the term of this patent is extended or adjusted under 35 U.S.C. 154(b) by 229 days.

(21) Appl. No.: 14/863,316

(22) Filed: Sep. 23, 2015

Related U.S. Application Data

(60) Provisional application No. 62/064,391, filed on Oct. 15, 2014.

(51) Int. Cl.
| | |
|---|---|
| A61B 5/00 | (2006.01) |
| A61B 5/103 | (2006.01) |
| A61B 5/11 | (2006.01) |
| A43B 17/00 | (2006.01) |
| A43B 3/00 | (2006.01) |

(52) U.S. Cl.
CPC .......... *A61B 5/1038* (2013.01); *A43B 3/0005* (2013.01); *A43B 17/006* (2013.01); *A61B 5/112* (2013.01); *A61B 5/1116* (2013.01); *A61B 5/1118* (2013.01); *A61B 5/6807* (2013.01)

(58) Field of Classification Search
CPC ... A61B 5/1038; A61B 5/1074; A61B 5/1036; A61B 5/112; A61B 5/1118; A61B 5/1116; A61B 5/6807; A43B 17/006; A43B 3/0005
USPC .............................. 73/865.4, 767, 772, 777, 73/862.041–862.044, 862.046, 172
See application file for complete search history.

(56) References Cited

U.S. PATENT DOCUMENTS

| | | | |
|---|---|---|---|
| 8,758,273 B2 | 6/2014 | Kubiak et al. | |
| 2005/0081623 A1* | 4/2005 | Frank | G01F 23/22 73/295 |
| 2008/0163670 A1* | 7/2008 | Georgeson | G08B 31/00 73/23.31 |
| 2012/0010535 A1 | 1/2012 | Kubiak et al. | |
| 2014/0260678 A1* | 9/2014 | Jentoft | G01L 5/16 73/862.046 |
| 2015/0096352 A1* | 4/2015 | Peterson | G01N 27/02 73/31.02 |
| 2015/0366471 A1* | 12/2015 | LeBoeuf | A61B 5/0059 600/301 |
| 2016/0066818 A1* | 3/2016 | Cowley | A61B 5/6807 600/592 |
| 2016/0195566 A1* | 7/2016 | Vock | A43B 3/00 73/514.01 |

* cited by examiner

*Primary Examiner* — Robert R Raevis
(74) *Attorney, Agent, or Firm* — Cooley LLP

(57) ABSTRACT

An in-shoe monitoring system has a shoe insert including a flexible substrate, force sensors secured to the flexible substrate, a position sensor and a motion sensor. A microcontroller is secured to the flexible substrate and is operational to receive sensor data from the force sensors, the position sensor, and the motion sensor. A wireless transceiver on the flexible substrate is operational to transmit sensor data from the force sensors, the position sensor, and the motion sensor. A portable computing device is operational to receive the sensor data from the wireless transceiver.

19 Claims, 14 Drawing Sheets

US 10,034,622 B1

IN-SHOE FOOT MONITORING UTILIZING AN INSERT

CROSS-REFERENCE TO RELATED APPLICATION

This application claims priority to U.S. Provisional Patent Application Ser. No. 62/064,391, filed Oct. 15, 2014, the contents of which are incorporated herein by reference.

FIELD OF THE INVENTION

This invention relates generally to human performance monitoring. More particularly, the invention is directed toward in-shoe foot monitoring utilizing an insert.

BACKGROUND OF THE INVENTION

There is a growing demand for metrics on human performance. Initial solutions are expensive, obtrusive and lack precision. Accordingly, there is a need for improved monitoring of human motion.

SUMMARY OF THE INVENTION

An in-shoe monitoring system has a shoe insert including a flexible substrate, force sensors secured to the flexible substrate, a position sensor and a motion sensor. A microcontroller is secured to the flexible substrate and is operational to receive sensor data from the force sensors, the position sensor, and the motion sensor. A wireless transceiver on the flexible substrate is operational to transmit sensor data from the force sensors, the position sensor, and the motion sensor. A portable computing device is operational to receive the sensor data from the wireless transceiver.

BRIEF DESCRIPTION OF THE FIGURES

The invention is more fully appreciated in connection with the following detailed description taken in conjunction with the accompanying drawings, in which.

Like reference numerals refer to corresponding parts throughout the several views of the drawings.

DETAILED DESCRIPTION OF THE INVENTION

Figure 1A:
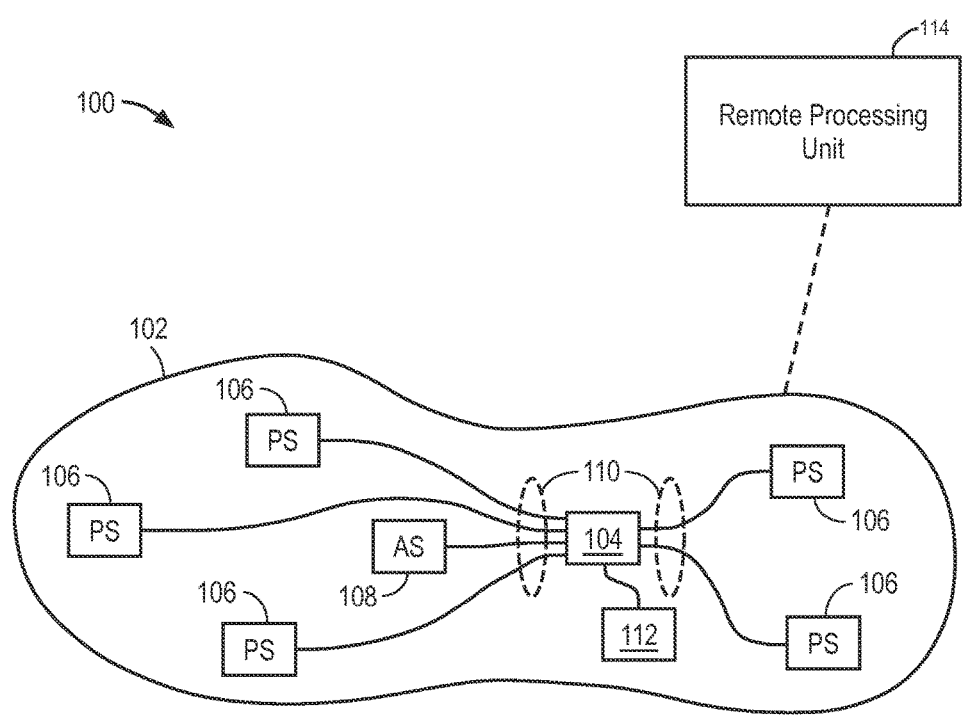
FIG. 1A is a top view of an apparatus configured in accordance with an embodiment of the invention.
Figure 2A:
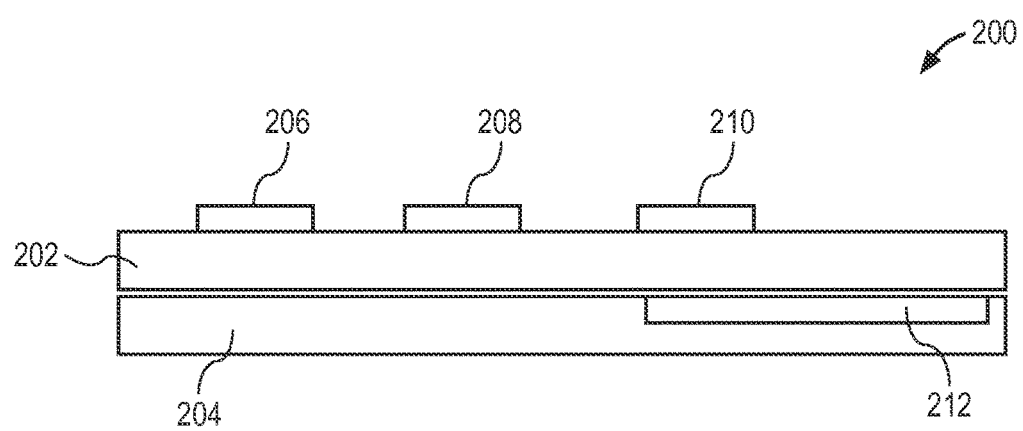
FIG. 2A is a side view of an apparatus configured in accordance with an embodiment of the invention.

FIGS. 1A and 2A illustrate in-shoe monitoring apparatus 100 according to embodiments of the invention. The in-shoe monitoring apparatus 100 includes a shoe insert 102. The shoe insert 102 (which can be referred to as Thin Platform Insert (TPI)) is configured to be relatively thin, such as less than about 3 mm, and is configured to be inserted into a shoe. The shoe insert 102 can be a single layer or multi-layer. The shoe insert 102 can be inserted under the insole used in regular shoes, specific sports shoes or boots, or specific rehabilitation shoes.

Once inserted, the shoe insert 102 provides a sensing platform in which data can be captured while a user utilizes the shoe. More particularly, as the user walks, runs, cycles, skis, hikes, and the like, the shoe insert 102 can capture data associated with the foot of the user. This data can be processed in real time and be analyzed to determine how the foot of the user is being utilized. The data can also be processed and analyzed to determine how the foot of the user is being affected by any external elements or instruments (e.g., insole, shoes, lace tightness . . . etc.). Specifically, the data can be processed to determine a pressure and force profile, orientation of the foot, muscle fatigue, shoe usage or lifetime, gait line, pedometer, calories consumptions, foot touch time, angular velocity, exerted forces, and the like. The user can be prompted by voice through a remote processing unit 114 (e.g., mobile device), or on the web by cloud analytics in real time for the users' coaches, trainers, colleagues, and others.

Figure 1B:
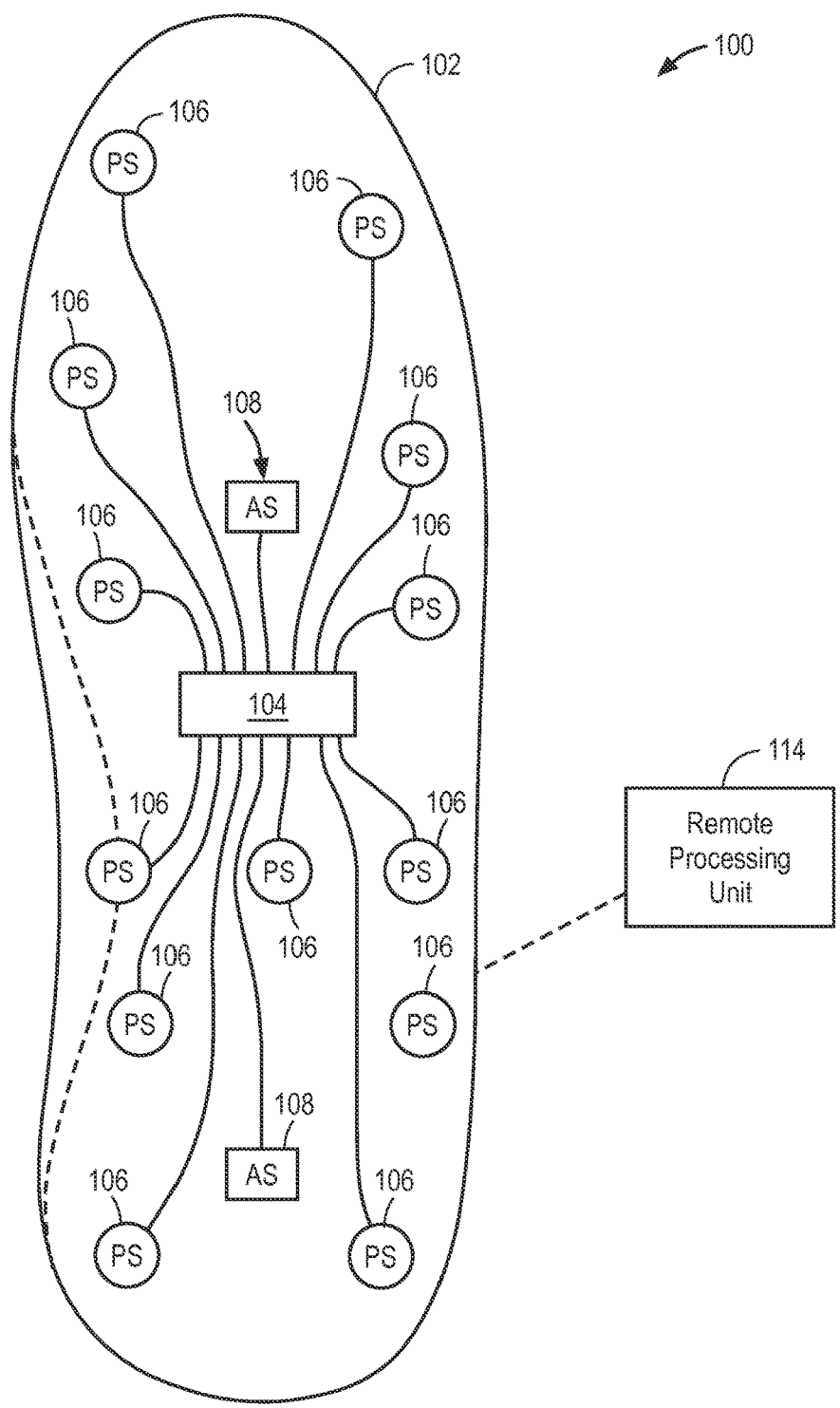
FIG. 1B is a top view of an apparatus configured in accordance with an embodiment of the invention.

The shoe insert 102 can act as a substrate for electrical components. As illustrated in FIGS. 1A and 1B, the shoe insert 102 can include a local processing unit 104, a plurality of force sensors 106, and one or more additional sensors 108. The one or more additional sensors 108 can include sensors to monitor position and/or motion. For example, the additional sensors 108 can include one or more accelerometers, one or more gyrometers, one or more magnetometers, one or more elevation sensors, one or more temperature sensors, one or more vibration components, and/or one or more heating elements, and one or more barometric pressure/force sensors matrix, solid state strain gauges, and/or one or more magnetometers, one or more humidity sensors, and/or one or more GPS components.

The force sensors are generally made of a polyester substrate, for example Mylar, and include a piezo-resistive material sandwiched between two polyester substrate layers and a separator. The force sensors commonly behave in a linear manner between force exerted and voltage output when connected to an operational amplifier (opamp) in a negative feedback configuration. The configuration usually has a feedback resistor and a negative voltage supplied to the positive input of the opamp. These two elements (feedback resistor and negative voltage) enable more control of the linear characteristics of the force sensor. Below reference is made to the feedback resistor as a digital potentiometer, which is automatically controlled by the processors for the best calibration of the linearity and range of the force sensor. The force sensors are designed for endurance; they achieve more than 20 million actuations in a lifetime. The size and location of the force sensors in the discrete or matrix forms are specially designed for the TPI. In general these force sensors have better than 2% linearity error, less than 2% repeatability error, less than 4% hysteresis, less than 10 microseconds of response time, and can operate in temperatures from −40 to +140 Fahrenheit. The linearity of the force sensors changes with temperature; therefore, the TPI has a temperature sensor to adjust and compensate for the temperature drift in the sensor's linear behavior.

Figure 8:
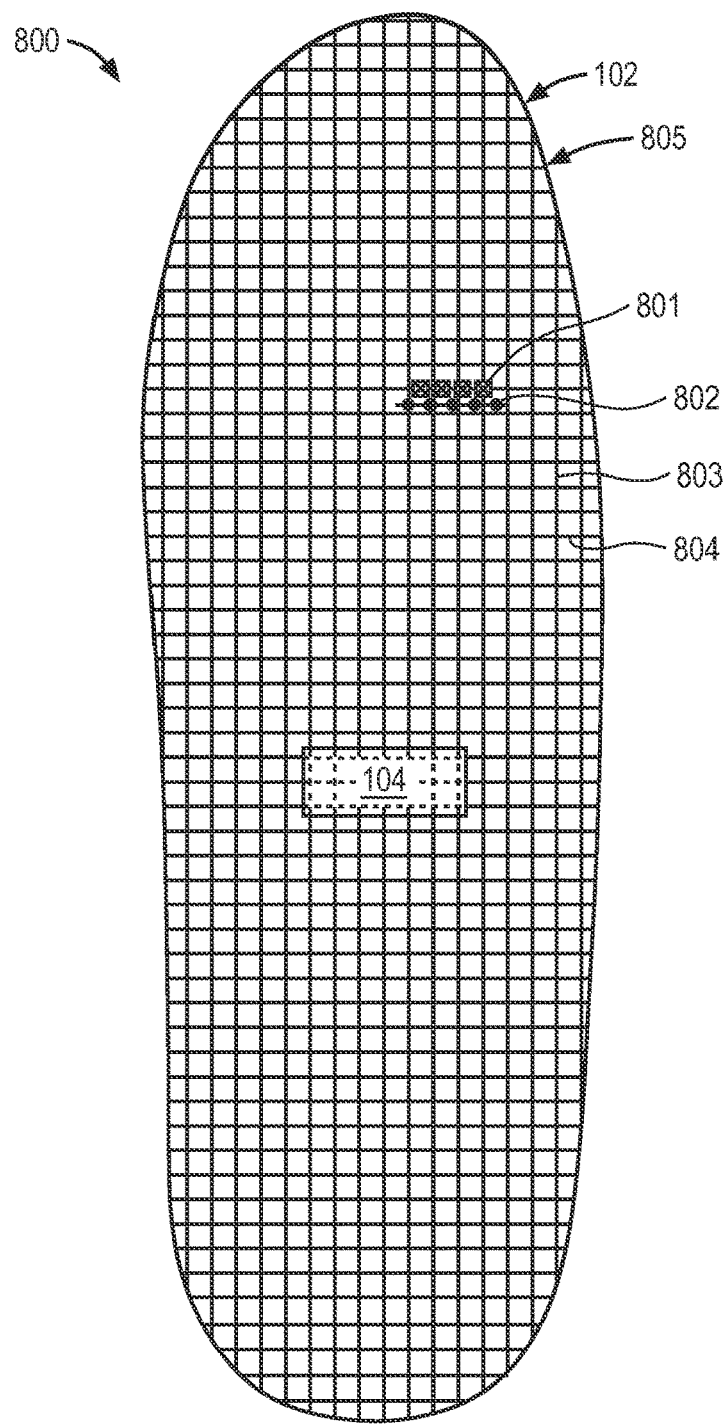
FIG. 8 illustrates an insert configured in accordance with an embodiment of the invention.

In one embodiment shown in FIG. 8, instead of individual discrete force sensors, a matrix of high resolution multi touch force sensors 801 provides high resolution data, e.g., on the order of 1000 samples per second or higher. In another embodiment this matrix of multi-touch sensors can be interleaved with a matrix of heating elements 802 to provide warmth to sportsman in winter days or for general comfort, barometric pressure/force sensors, and/or solid state strain gauges. In one embodiment, these matrices of sensors are connected using silkscreen thin wires 803 and 804. The one or more additional sensors 108 can, for example, provide position and/or motion sensors that can be used to determine location or orientation of a user's foot and other sensing functions. The shoe insert 102 can also include wiring, silk screen embedded wirings, or cables 110 for electrically connecting the force sensors 106 and the additional sensors 108 to the local processing unit 104.

The shoe insert 102 can also include a battery 112. The battery 112 can be electrically coupled to at least the local processing unit 104 to provide power thereto. The battery 112 can be rechargeable. In one embodiment, the battery is thin and is rechargeable. In one embodiment, the battery is protected with a film of fireproof PVC, fiberglass and other materials or combinations thereof. A thin battery made of solid state material is used in one embodiment.

In addition, the in-shoe monitoring apparatus 100 can include a remote processing unit 114. The remote processing unit 114 may be a portable electronic device, which is typically associated with the user. For example, the remote processing unit 114 can be a computing device, such as a smartphone, a tablet computer, a personal computer, a notebook computer, an electronic watch, an electronic headset, and the like. The shoe insert 102 can transmit data to the remote processing unit 114, and can also receive data from the processing unit 114. Additionally, the remote processing unit 114 could also be used to configure operation of the electrical components that are part of the shoe insert 102. The transmission of data and/or commands between the local processing unit 104 and the remote processing unit 114 can be performed in a wireless or wired manner using low energy Bluetooth and/or ANT+.

Another embodiment of an apparatus 800 is shown in FIG. 8. In this case the force sensors 801 are at the intersection of two horizontal and vertical silk screen wires or cables 804 and 803 respectively, every intersection of the wires or cables 803 and 804 there can be a force sensor which will produce thousands of those force sensors and provide high resolution of the foot force profile and other data. Also, there can be a micro-heating element 802 used to provide heating, solid state strain gauges, or barometric pressure/force sensors for the foot in case it is cold weather or for other needed reasons. Other electronic components for the apparatus 800 can be similar to those in FIG. 1.

Figure 2B:
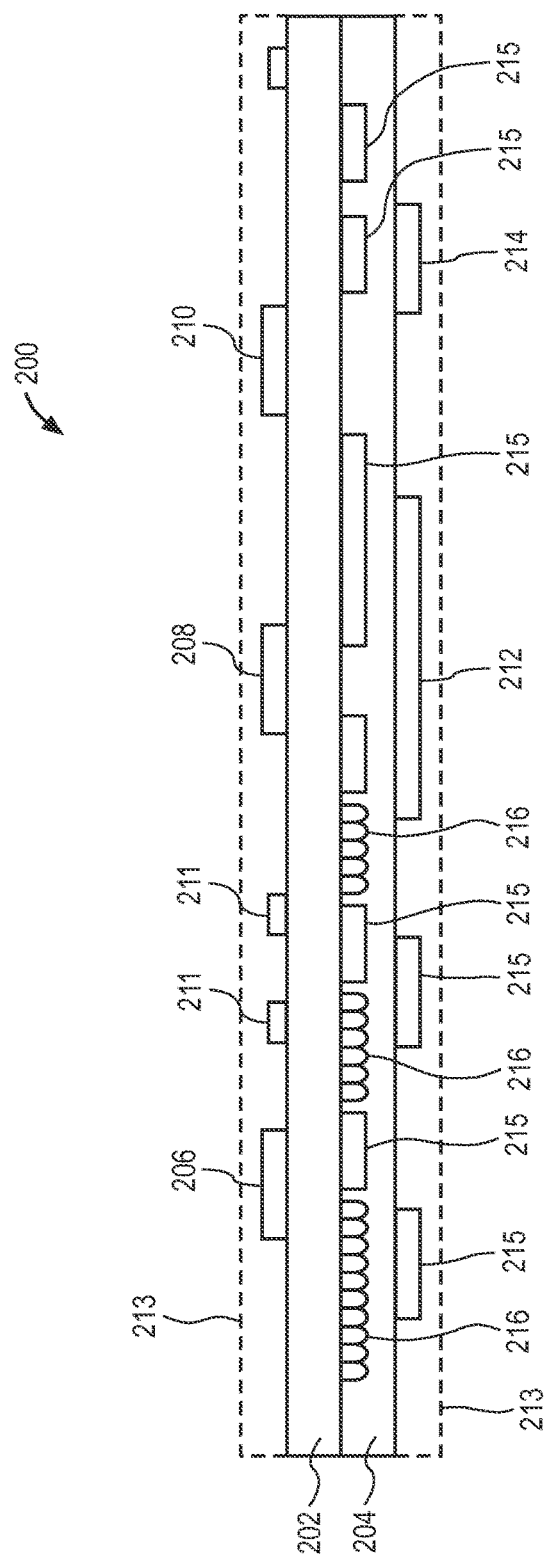
FIG. 2B is a side view of an apparatus configured in accordance with an embodiment of the invention.

FIGS. 2A and 2B are cross-sectional views of a multi-layer insert 200 according to two embodiments of the invention. The multi-layer insert 200 includes an upper layer 202 and a lower layer 204. The upper layer 202 and the lower layer 204 are typically stacked on one another and are secured together by an adhesive or other means. In this embodiment, the upper layer 202 can include electrical components 206, 208 and 210, which correspond to the components in FIG. 1. The upper layer 202 can also include wires (e.g., silk screen embedded wires) or cables (not shown) that interconnect the electrical components 206, 208 and 210. The bottom layer 204 can include other electrical components, such as a battery 212. The battery 212 can supply electrical power to the electrical components 206, 208 and 210 as well as any electrical components in the bottom layer 204. The multi-layer insert 200 can also include a thin protective layer 213, and force sensors 211. Also, the bottom layer 204 can have other components for energy harvesting 214 (energy harvesting electronics) and 215 (energy harvesting sensor) which will enable the user to generate electrical charging current to the battery 212 and hence constitute a self-charging device. Component 216 may include electronics and coils for wireless charging. Energy harvesting can increase the time usability of the device and can reduce the number of times the device needs to charge. This can be achieved by adding a matrix of high efficient piezoelectric fibers, ceramics, or other types into specific energy harvesting electronics. In addition, the bottom layer 204 can also include wireless charging electronics and coils to enable the user to charge the device without the need to connect it to a cable, although direct cable charging can also be part of the electronic device.

Figure 3:
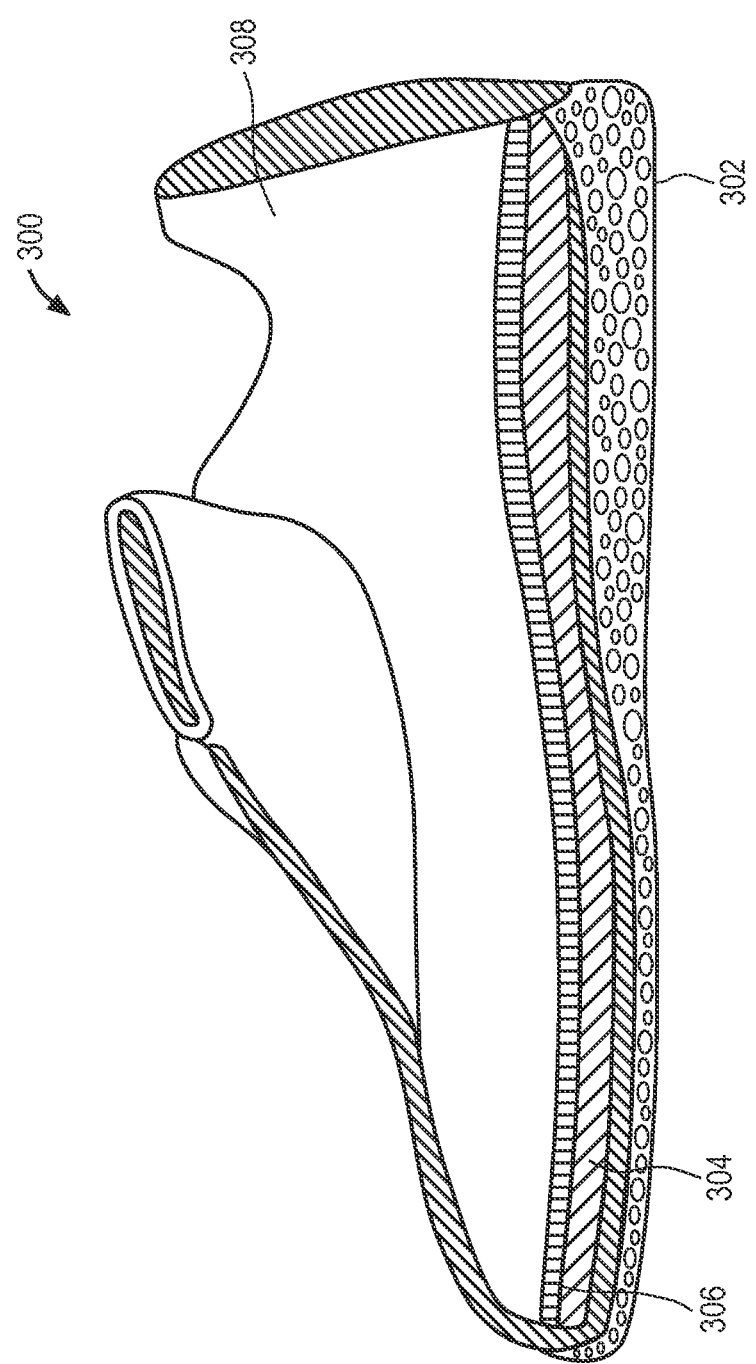
FIG. 3 illustrates a shoe incorporating an insert associated with an embodiment of the invention.

FIG. 3 is a cross-sectional side view of a shoe 300 (or other footwear) according to one embodiment. The shoe 300 includes a sole 302, an insert 304 and an insole padding layer 306. The insert 304 is provided within the shoe 300 between the sole 302 and the padding layer 306. The shoe 300 also includes an upper region 308. By providing the insert 304 within the shoe 300, the insert 304 is properly positioned to monitor the user's foot during various activities, such as walking, cycling, golfing, running etc. In one embodiment, the insert 304 can be the shoe insert 102 illustrated in FIG. 1. Since the insert 304 need not touch the person's foot, the long term durability of the insert 304 is not compromised and user experience is improved.

Figure 4:
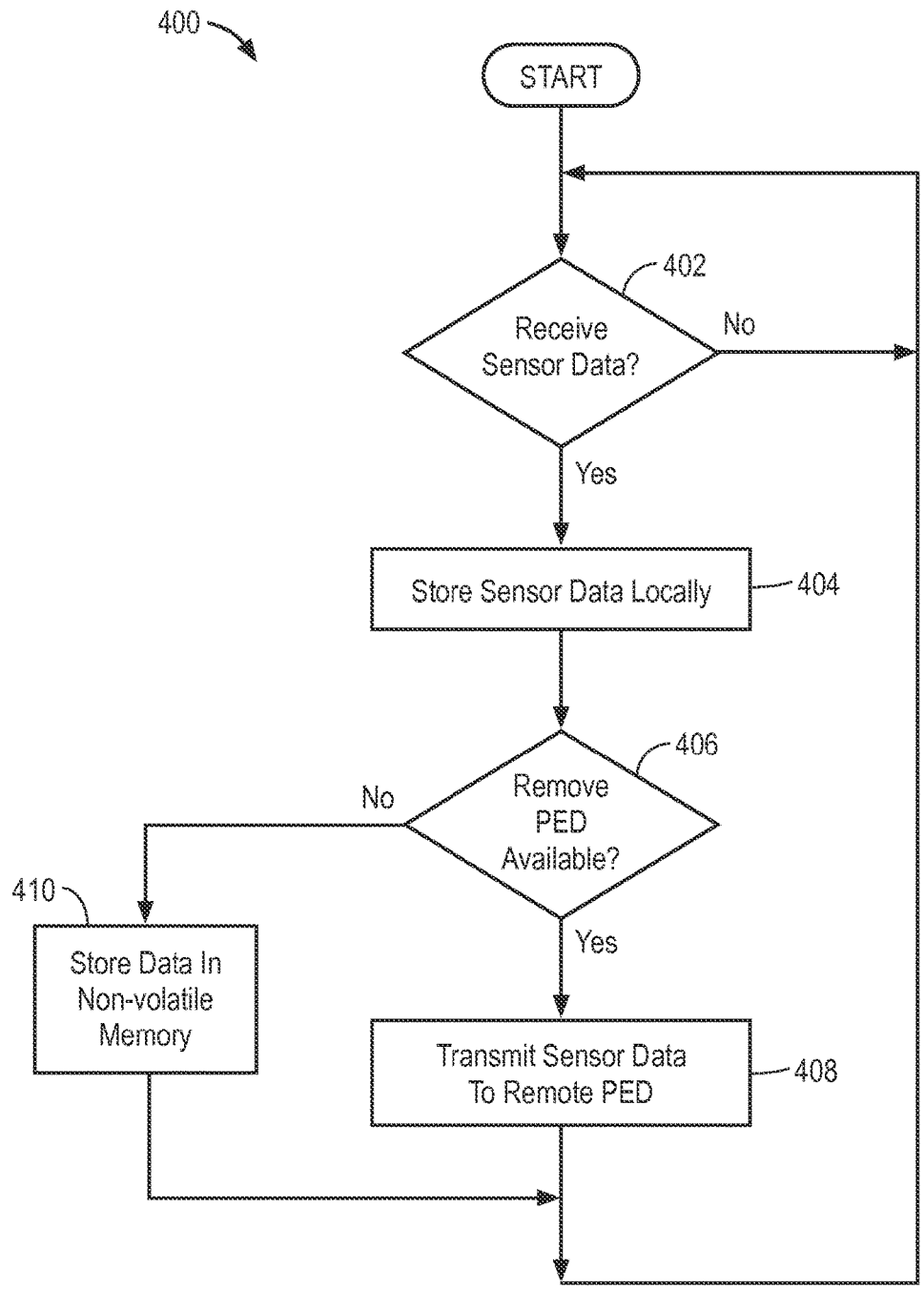
FIG. 4 illustrates processing operations associated with an embodiment of the invention.
Figure 10:
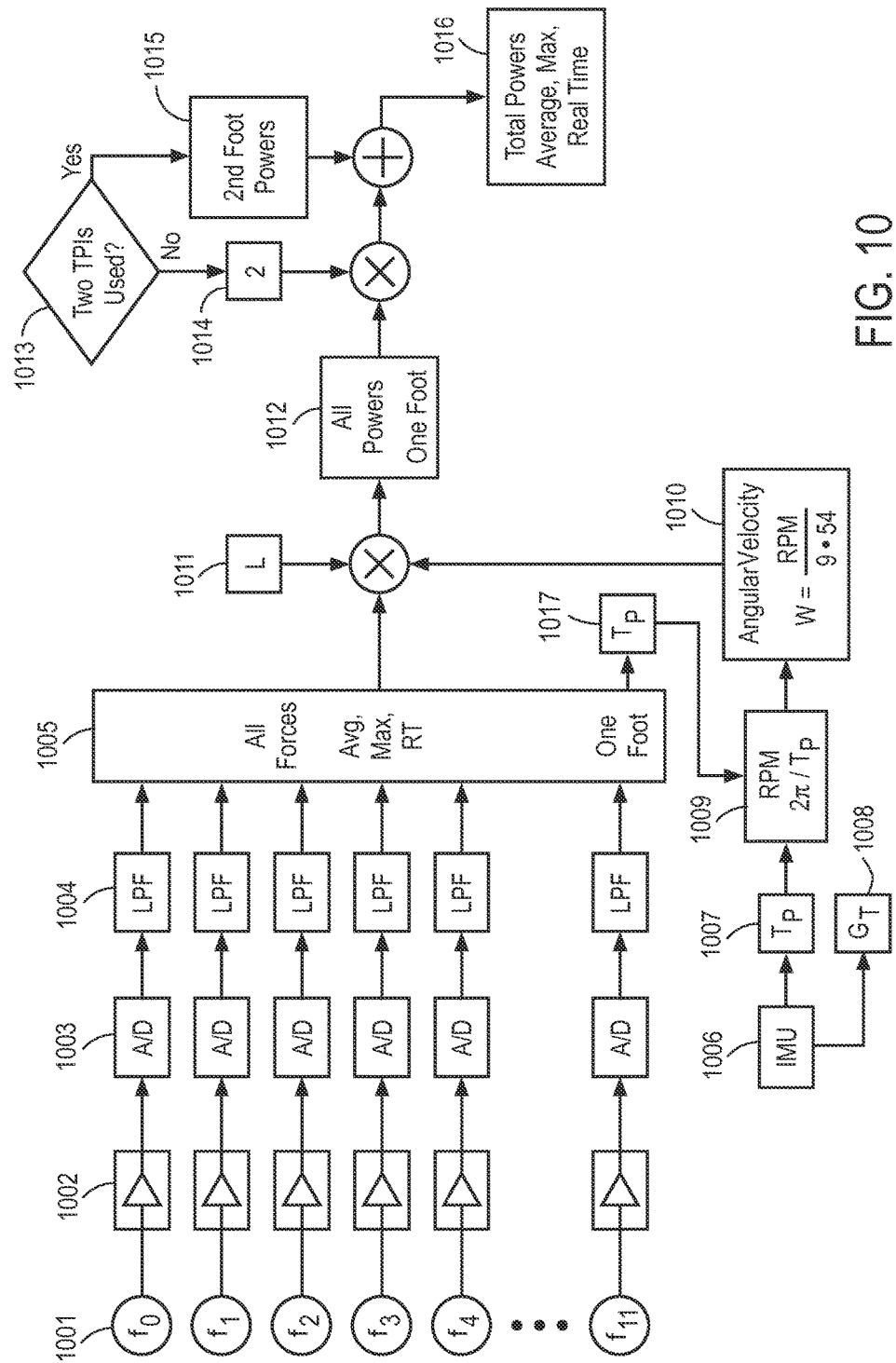
FIG. 10 illustrates circuitry utilized in accordance with an embodiment of the invention.

FIG. 4 is a flow diagram of a data acquisition process 400 according to one embodiment. The data acquisition process 400 can be performed by an electronic shoe insert, such as the shoe insert 102 illustrated in FIG. 1 or the multi-layer insert 200 illustrated in FIG. 2. More specifically, the data acquisition processing 400 can be performed by a local processing unit, such as a microcontroller (or microprocessor), provided on or integral with the shoe insert. Additional detailed data acquisition and processing flow using TPI's software and hardware is described in connection with FIG. 10.

The data acquisition process 400 can begin with a decision 402 that determines whether sensor data has been received. When the decision 402 determines that sensor data has not been received, then the data acquisition process 400 awaits the receipt of sensor data. For example, the sensor data can be provided by one or more sensors provided on or integral with the shoe insert. On the other hand, when the decision 402 determines that sensor data has been received, the sensor data can be stored 404 locally. Hence, this can enable the processor to only wake up and consume battery power when the sensors are active and sensing activity, this way battery life can be improved. Next, a decision 406 can determine whether a remote portable electronic device is available. The remote portable electronic device is typically a personal electronic device that is associated with the user of the electronic insert. Examples of a remote portable electronic device include a smart phone, a tablet computer, a laptop computer, personal computer, an electronic watch, and the like. When a remote portable electronic device is available, then the sensor data that has been obtained can be transmitted 408 to the remote portable electronic device. The transmission 408 can be by wireless communication between the electronic insert and the remote portable electronic device. In this regard, the shoe insert would include a wireless interface. Alternatively, when the decision 406 determines that a remote portable electronic device is not available, the data can be stored 410 in nonvolatile memory, so that the data remains available for later transmission to a remote portable electronic device, when such a device becomes available.

The sensor data once acquired from electronic shoe insert can be processed to correlate and analyze the data so that it is more useful for monitoring, examining, recording and presenting information on a user's foot usage in real time and/or in real life out in the field scenarios.

Figure 5:
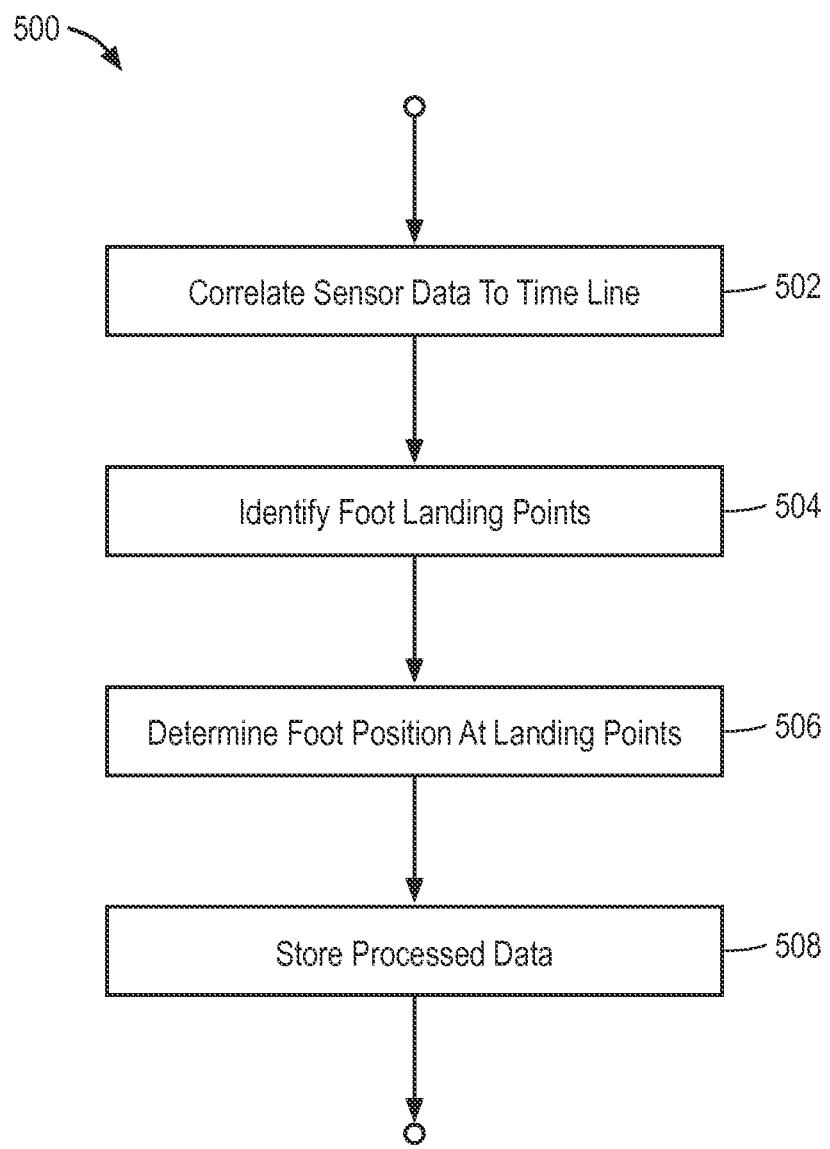
FIG. 5 illustrates processing operations associated with an embodiment of the invention.

FIG. 5 illustrates a flow diagram of data processing 500 for runners as an example according to one embodiment. The data processing 500 pertains to certain processing that can be performed either locally or remotely, or some combination of both, by processing circuitry (e.g., local processing unit 104; remote processing unit 114; or cloud processing unit 115).

The data processing 500 correlates 502 sensor data to a timeline. Next, the sensor data can be analyzed to identify 504 foot landing points. Additionally, the data processing 500 can determine 506 foot position at the landing points. The foot position can pertain to relative location of the foot and/or orientation of the foot. Thereafter, processed data that has been produced by the data processing 500 can be stored 508. The stored processed data 508 can be subsequently further processed and/or presented to an interested person. The further processing can include computing a force profile, orientation of the foot, angular velocity, muscle fatigue, shoe usage or useful life, gait line, etc. More importantly, data from the sensors can be aggregated and correlated to get an exact understanding of the specific behavior of the foot biomechanics (e.g., is the foot over-pronating, supinating, landing with extreme g-forces, landing in mid-foot, back or forefront . . . etc.).

The locality of the processing by the local processor, the PED processor, or cloud processor can be decided on a dynamic basis based on continuous hand shake and metadata exchange between the two processors to decide who will process the data based on available resources (like memory, threads . . . etc.) and based on the battery charge condition of the respective batteries of the devices. The design and architecture of using different processors can happen dynamically while the code and the device are running. This can also be done during static compilation of the code, where the code itself can be written in different languages and provided with APIs to talk in different languages. This dynamic or static aspect can result in a large improvement in user experience related to battery life and responsiveness.

Figure 6:
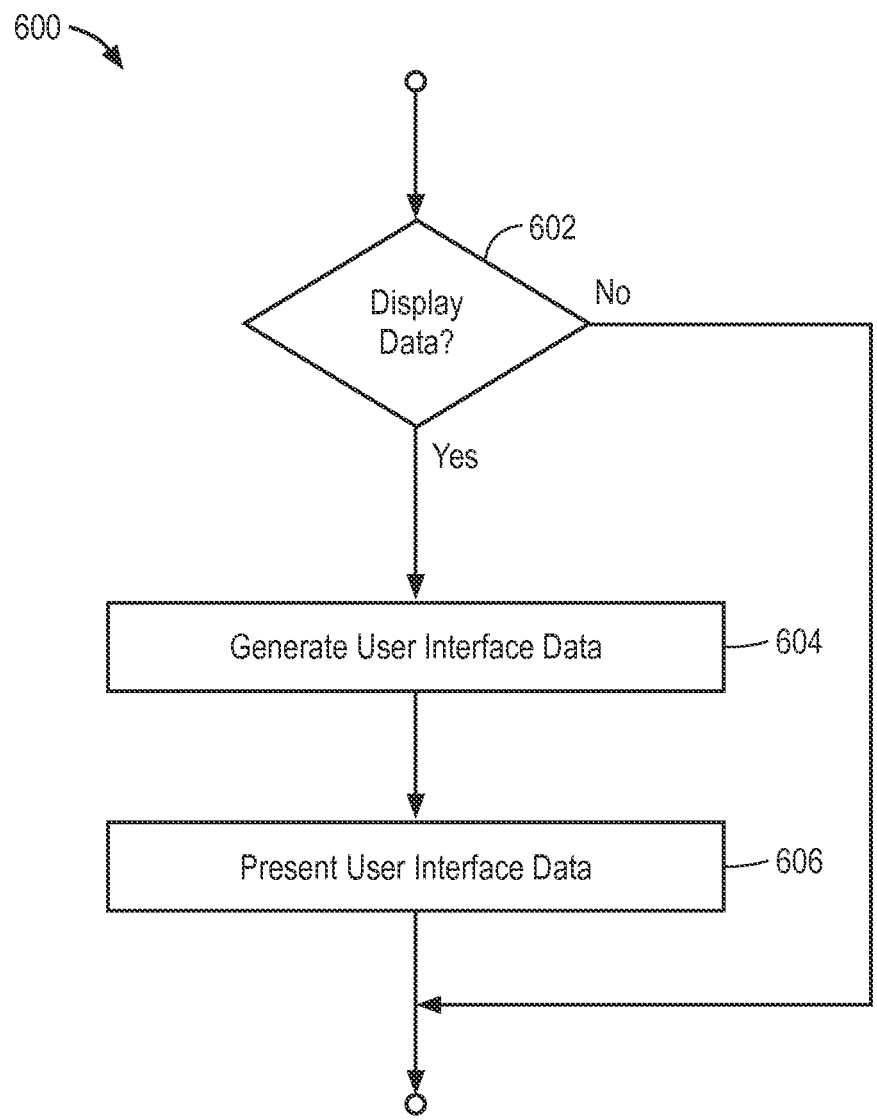
FIG. 6 illustrates display processing operations performed in accordance with an embodiment of the invention.

FIG. 6 is a flow diagram of data display process 600 according to one embodiment. The data display process 600 is processing that can be utilized to present a user interface to an interested person concerning the evaluation of the foot usage by the in-shoe monitoring apparatus.

The data display process 600 illustrated in FIG. 6 can begin with a decision 602 that determines whether data is to be displayed based on user selection or other critical activity events. When the decision 602 determines that data is to be displayed, user interface data can be generated 604. Next, the user interface data can be presented 606. The user interface data can be presented 606 by displaying the user interface data on a display device. For example, the remote processing unit 114 illustrated in FIG. 1 can include a display device on which the user interface data can be presented 606. On the other hand, when the decision 602 determines that data is not be displayed, the data display process 600 can bypass blocks 604 and 606 since no user interface data needs be generated or presented. Once sensor data has been acquired and potentially processed or preprocessed, the processed data is available for further evaluation on PED, cloud, or other platform.

Figure 7:
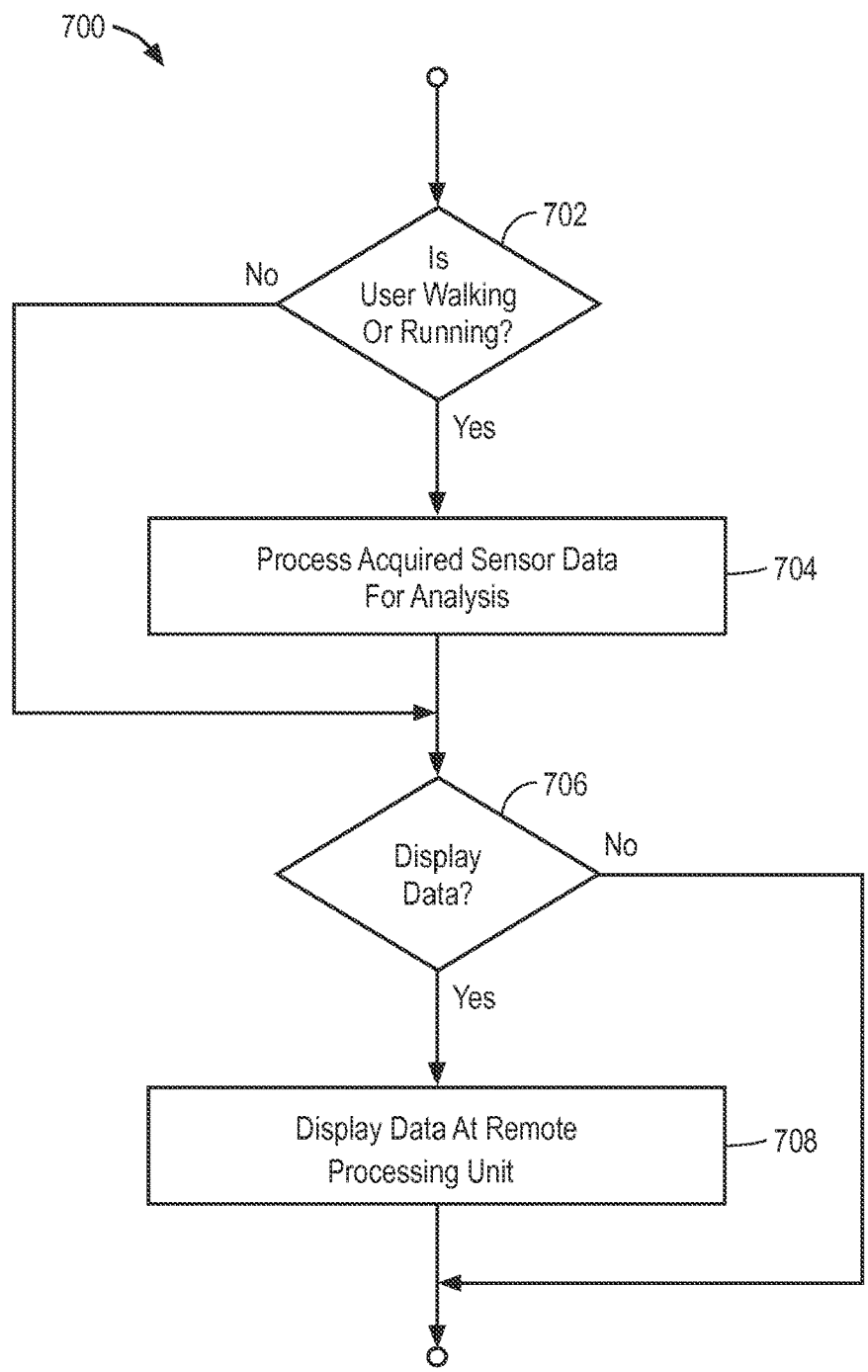
FIG. 7 illustrates processing operations associated with an embodiment of the invention.

FIG. 7 illustrates a flow diagram of data processing and display process 700 according to one embodiment. Generally speaking, the data processing and display process 700 automatically examines sensor data to determine whether a user is walking, cycling, or running (i.e., a specific user activity or activities) and, if so, the data can be processed so that data can be displayed to the user.

The data processing and display process 700 can begin with a decision 702 that determines whether a user is active (i.e., walking, cycling, or running). In this embodiment, it is assumed that the user is utilizing the electronic insert to monitor their foot usage during the user activity. Hence, in this embodiment, the data of interest from the electronic shoe insert is data concerning user activity, such as walking, cycling, or running. Hence, when the decision 702 determines whether the user is walking, cycling, or running, the acquired sensor data is processed 704 to support additional analysis. Next, a decision 706 determines whether data is to be displayed. When the decision 706 determines that data is to be displayed data, the data can be display 708 at a remote processing unit. In one implementation, the data displayed 708 at the remote processing unit is data that is captured by the electronic shoe insert and then wirelessly transmitted to the remote processing unit where it can be displayed on a display device. The data capture and display can be processed in effectively real-time on PED or cloud, if so desired. Alternatively, if the decision 702 determines that the user is not active any sensor data associated with the electronic shoe can be discarded.

If the decision 706 determines that data is not to be displayed, then the block 708 can be bypassed. The data processing and display process 700 illustrated in FIG. 7 can be used to present feedback data to a user as they are active (e.g., walking, cycling or running). The feedback data can be presented in near real-time.

Figure 9:
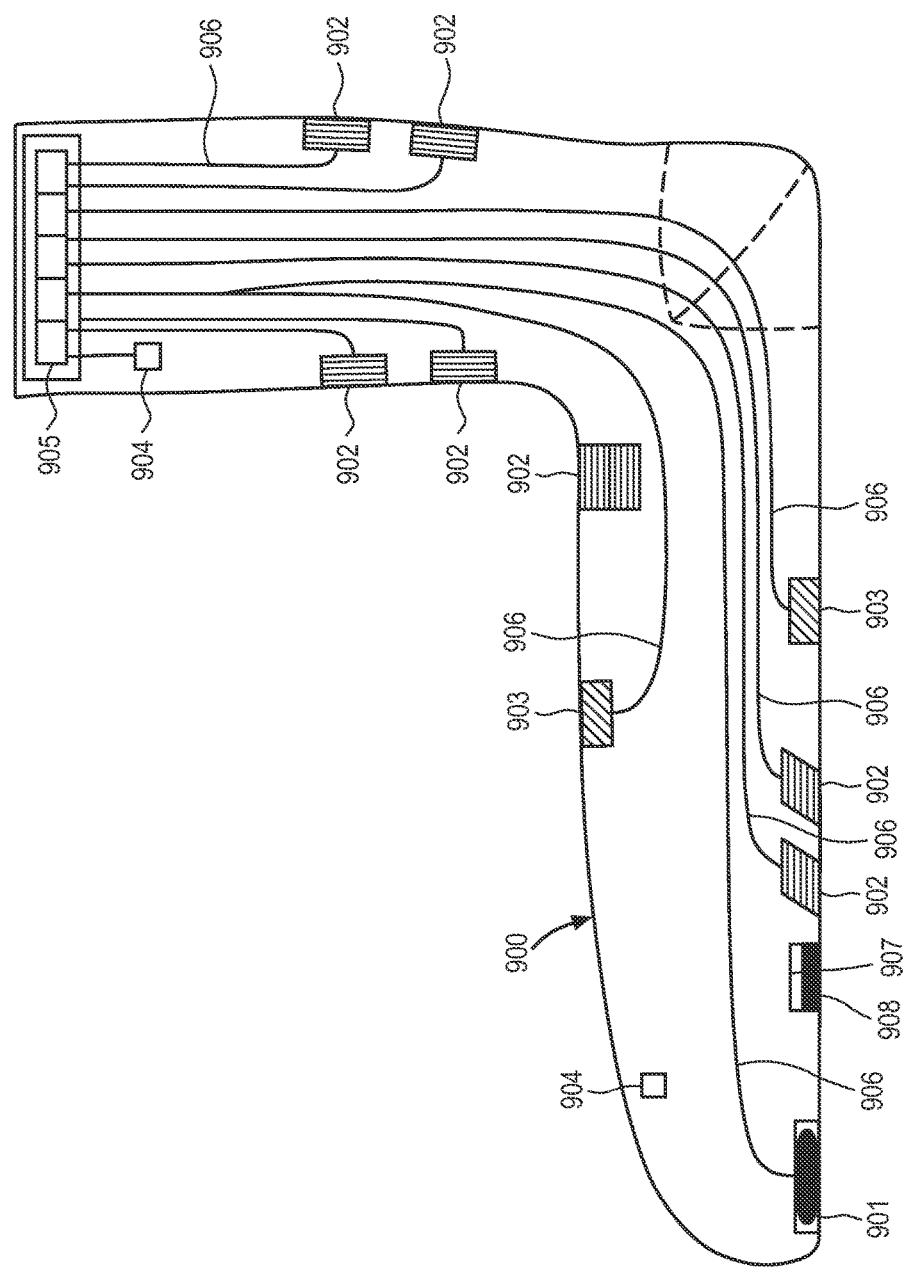
FIG. 9 illustrates a sock configured in accordance with an embodiment of the invention.

As shown in FIG. 9, in another embodiment, foot usage monitoring can be achieved using a sock instead, or in addition to, a shoe insert. The sock is an electronic sock that can include one or more sensors 902 and processing circuitry 901. Other sensors 903 may include one or more hydration sensors, EMG sensors, humidity, temperature, force, orientation, blood oxygen, blood glucose level, and/or heart rate sensors. Processing unit 905 is on a flexible PCB 904. Additional components may include an accelerometer, gyrometer, or magnetometer. Conductive threads 906 connect all sensors to the processing unit 901.

In another embodiment the TPI is used to measure outdoor and indoor cycling power, cadence, derivatives of power, g-forces, angular velocity, biomechanics of the foot across every revolution, potential injury occurrence, and other parameters. In this scenario the TPI hardware, firmware, software, and accessories operate as follows.

In one embodiment, firmware negotiates a Dynamic Processing Protocol (DPL) with the mobile device and the cloud. If a mobile device is not present then firmware on the device will perform full computations and necessary analysis until the mobile device becomes present and connected to the TPI device. This is called DPL-0 (DPL level 0). In other cases where a PED mobile device is present and TPI decides to share the computation with the mobile device, this is DPL-1. In the case where all three computing nodes, TPI, PED, and cloud are sharing computations this is DPL-2. The negotiation is based on presence of all three devices, how much battery charge level is in TPI and PED, and how much processor usage is being consumed on the three nodes, and user preference to have immediate feedback on the exercise or not, and many other criteria.

Firmware detects pressure and movement and starts the wake up process of the processor and the circuitry. Most of the following steps are referenced in FIG. 10. To detect force and pressure firmware will use the force sensors 1001. These are either multiple discrete force sensors or a matrix of force sensors.

The user can perform calibration by standing on one foot 3 times or less at a time (in case user is wearing two TPIs in each foot). Firmware calculates the needed parameters for the linearity of the force sensors by controlling digital potentiometer in the op-amp circuitry 1002. The firmware also supplies voltage to the op-amp. Firmware will identify the best linear curve and the max values and program the components accordingly for the best accuracy for the user case. TPI firmware will also do dynamic offsetting and calibration during the exercise when the TPI and force sensor are momentarily not used and/or pushed on.

Firmware will perform either a classical Low pass Filtering (LPF) or Nth degree polynomial regression/interpolation on every analog input coming from the force sensors and other applicable sensors similar to LPF in hardware 1004. Also firmware enables the LPF for the gyro on the IMU chip and all corresponding filters for the other IMU sensors as shown with block 1006 (Accelerometer and Magnetometer). Firmware will also collect data of g-forces the foot is creating during each revolution by using the accelerometer as shown in block 1008. The same accelerometer also detects acceleration at the pull-up phase of the foot from the 6 pm position to roughly the 10 pm position of a revolution. This acceleration is interpreted to calculate an estimate of how much pull-up force the foot is generating and hence estimate the pull-up power. The gyro can also improve the estimated pull-up force measurement by detecting the angular speed in addition to the measured acceleration. It is also possible to do the force sensors LPF in the hardware connected right after the op-amp circuitry as shown with block 1004. Also it is possible to build a specialized ASIC which includes many of the hardware components (i.e. op-amps, digital potentiometers, LPFs, ARM, BLE, ANT+, power electronics, DPL protocol . . . etc.)

Firmware will collect digitized values of 6 discrete force sensors or more than 800 micro-sensors in matrix form as analog inputs from the A/D registers as shown in block 1005.

In the case of bicycling, firmware keeps track of the beginning of the revolution (starting at 0 o'clock and back to 12 o'clock) using the accelerometer and gyrometer data collected through the revolution. A/D resolution will be 12 bits or higher. The fixed sampling rate is to be at 1 KHz (sample/sec) for each force sensor at 10 KHz or higher (i.e. 6 discrete sensors will be at 60 KHz). Firmware will perform three separate acquisitions and calculations. First, sampling optimization can be performed based on variable or fixed sampling. Variable slices are based on the cyclist cadence (Revolution per Minute RPM) slice or range. Sampling rate changes are applied by firmware at every 5 RPM increase. Sampling will be at 10,000 (or higher) than the RPM (i.e., if RPM was 60, hence there will be 1 RPS (Rev per sec), and in this case number of samples equal 1 RPS*10,000=10,000 samples taken per sec (per one revolution) per each force sensor (one sample every 100 microseconds, called time sample interval Ts), then 10,000*6 sensors=60,000 samples/sec. When a new range/slice is reached (i.e. 65 RPM) then new sampling is applied. If RPM is below or equal to 10, then sampling rate will be maintained at 2500 sample/sec (400 microsecond interval)—which is equivalent to 15 RPM sampling rate.

Fixed sampling is at 60 microsecond intervals or lower (i.e., 16.67 KHz or higher), hence equal 16.67 KHz (sample/sec) for each sensor; hence for six sensors the total sampling rate is 100 KHz. Average each sampled digitized force analog input value across each and every revolution (F0, F1, F2 . . . F5 . . . etc. averages) as shown in 1005. Acquire the 5 highest values of each discrete force sensors and micro-sensors as shown in 1005. After acquiring the same or equivalent sampling from gyrometer and accelerometer, power is calculated at every time interval (micro or milliseconds). This provides a clear power profile across the cycling revolution as shown in block 1012.

During the cycling revolution and using the accelerometer the angle of the foot is observed on every time interval to calculate the tangential (useful) and internal (not useful—pushing towards the crank arm) forces to present to the user the power exerted and loss (Applied force efficiency per rev). This information is important to present to the user if the position of these forces can be an impact on the user's ankle, knee, muscles, heel or other areas.

Firmware will convert each of the digitized values into Force value in Newton (using a predetermined linear equation provided by the linear calibration of the op-amp circuitry Force0(N)=a*(digitized Voltage0)+b)—where b could be a designed offset or pre-calculated noise as shown in block 1002.

Firmware will do a summation of all the forces' sensors in Newton for each time sample interval (Ts) and the average values across one revolution. This will result in Total_F(Ts) and Total_F(avg/rev) respectively in Newton exerted for a specific Ts and across a revolution respectively as shown in block 1005.

Although RPM and Angular velocity (Av) can be reliably calculated by the gyro only for cycling scenarios, the firmware will also include the accelerometer measurements and force wave signals for highest accuracy as shown in blocks 1006 and 1007. We have found and created a new method of measuring Av and RPM using the gyro by observing the natural movement of the oscillating movement of the cycler foot around one revolution. This oscillating movement is in the form of pitch movement (not roll nor yaw) going into positive and negative regions of the angular velocity and producing almost a perfect sine-wave with a time period called Tpg as shown in block 1007. We have also found and created a new method of measuring Av and RPM using the force sensors by observing the natural movement of the oscillating action of the cycler foot around one revolution. This oscillating movement is in the form of a sine wave, going into positive and zero or slightly negative regions of the angular velocity and producing a time period called Tpf as shown in block 1017.

The sine wave values are the representation of how fast the foot is pitch-oscillating across one revolution. If the pitch oscillation is not uniform, then the cyclist is not exerting the best possible aligned push on the pedal and hence a notification will be presented to the user. This non-uniform movement of the foot might lead alone or in association with other observations into ankle or knee injuries.

The firmware also calculates the time interval angular velocity Av_ts (based on Ts ticks) using the gyro and accelerometer. The firmware also calculates the angular velocity Av(avg/rev) and RPM using the duration time period (Tp) across the whole revolution as shown in block 1010. Tp produces the cadence by calculating the RPM for that revolution (RPM=Cadence=2*pi/Tp), and hence Av_rev=RPM/(9.549296586) as shown in block 1010. Also Av is represent the Ts tick angular velocity which to be used later to calculate power in conjunction with Total_F(Ts).

Assume two cases where the cycler is wearing on TPI or two TPI. In case of one TPI the calculation of power produced will be multiplied by 2 as shown in block 1014 to include the other foot that doesn't have the TPI. In the second case where user has two TPIs then each foot power is measured separately and summed together for total power applied as shown in blocks 1015 and 1016.

Firmware will compute the above values using the following equation Power(Ts)=Total_F(Ts)(Newton)*L(meters)*Av_ts(rad/sec) representing the power profile across every Ts time tick during the revolution and every revolution as shown in block 1012. L is the crank arm length as shown in block 1011.

Firmware calculates the Total Power(avg/rev)=2*Total_F(avg/rev)(Newton)*L(meters)*Av(avg/rev)(rad/sec) as shown in block 1012. This represents the total average power exerted in each revolution. Overall Power average of the whole ride is calculated and other derivative of power is calculated as shown in block 1012.

Firmware sends both the RPM (cadence) value and Power to the mobile app for the revolution that just took place based on the selected option in the app—i.e. RT=real time. However, if the setting is set to 5 sec or 10 sec, then firmware will average across 5 sec or 10 sec and then send the data of cadence, power and the rest to the mobile app.

From Total_F(Ts) and Power(Ts) Firmware will be aware where the foot is at very small intervals (at least for each one degree across the whole revolution—hence 360 deg=360 times). Firmware will be able to save all the necessary and minimum data collected into a flash on the TPI.

Firmware will fetch temperature, humidity, and elevation sensors values and use it for analog and other components values compensation for highest accuracy. Firmware uses two communication protocols, ANT+ in addition to BLE.

In the case where the mobile device is not available even after the cyclist or runner had finished their ride or run, and the user puts the TPI and shoes on the wireless charging base (WCB). Firmware will be aware when the TPI battery is being charged in wireless mode, at this event firmware has the option to connect through BLE to the wireless charging base (WCB) and send all necessary ride, run, exercise data that was saved on the flash memory chip to WCB. In this case WCB is always connected to the user personal WIFI network, and it will transmit all the saved exercise data on the TPI device to the cloud processing unit for computation, analysis and display. Hence the user can go directly to their PC, tablet, and other devices to see the ride, run, or any exercise they just finished. All data from the device to mobile device to the cloud are encrypted in all directions for security and privacy.

Based on the forces produced above, the base force level produced by the cyclist in a sitting position when cycling and the lateral acceleration swing produced by the accelerometer, the firmware will be able to know if the cyclist is sitting or standing while cycling. When two TPIs are used by the cyclist in each foot, the firmware and applications will be able to show the differential efforts and power produced by the cyclists for each foot. Power derivative for both feet (Torque efficiency, pedal smoothness and other) may also be computed.

An aspect of the invention is a mobile application. The mobile application is designed for simple presentation of data to avoid overwhelming the user. Data includes power, cadence and a RGB notification for all items listed below. If user prefers to learn more, s/he can dive down into more details in other pages by clicking on the interested parameter.

The application performs a DPL protocol negotiation to decide with the TPI device, cloud on which DPL level and responsibilities will be established for each computing point. The application enables first time users to input their personal data and accept a EULA. The application may perform the following computations:

a. Real time Power, Average Power, Normalized power, Maximum power b. Real time Cadence, average cadence, maximum cadence c. Torque efficiency, pedal smoothness d. G-forces exerted by the foot during the cycling e. Foot force profile, heat map of the most forces for across the foot f. Foot orientation in real time and in trend across a ride g. Notification related to ankle, knee potential injuries h. Tangential and vertical forces across the revolution and overall across the ride i. Lost power and exerted power j. Potential foot movement across the pedal or inside the shoe k. Shoe lifetime analysis l. Insole lifetime analysis m. Present advertisements only on tablets (not phones)

n. Enable user to do the following;

i. Calibrate the TPI device ii. To switch between real-time, average of 3 sec, 5 sec, and 10 sec for all displayed cycling parameters iii. To enable/disable logging for debugging purposes iv. To enter user data related to age, weight, crank length (L), zip code/location, and other necessary personal information v. Ability to purchase merchandise vi. Connecting to TPI use BLE vii. Dive into more details by showing graphs and detailed analysis about user ride viii. Ability to send stream of the cadence, power and other information in real time to user's coach, trainer, friends or others directly or through the social environment on the web page.

ix. Start/stop logging, and share logging files on email, and other mediums. Keeping the last 10 log files on the phone.

b. and other related information

Figure 11:
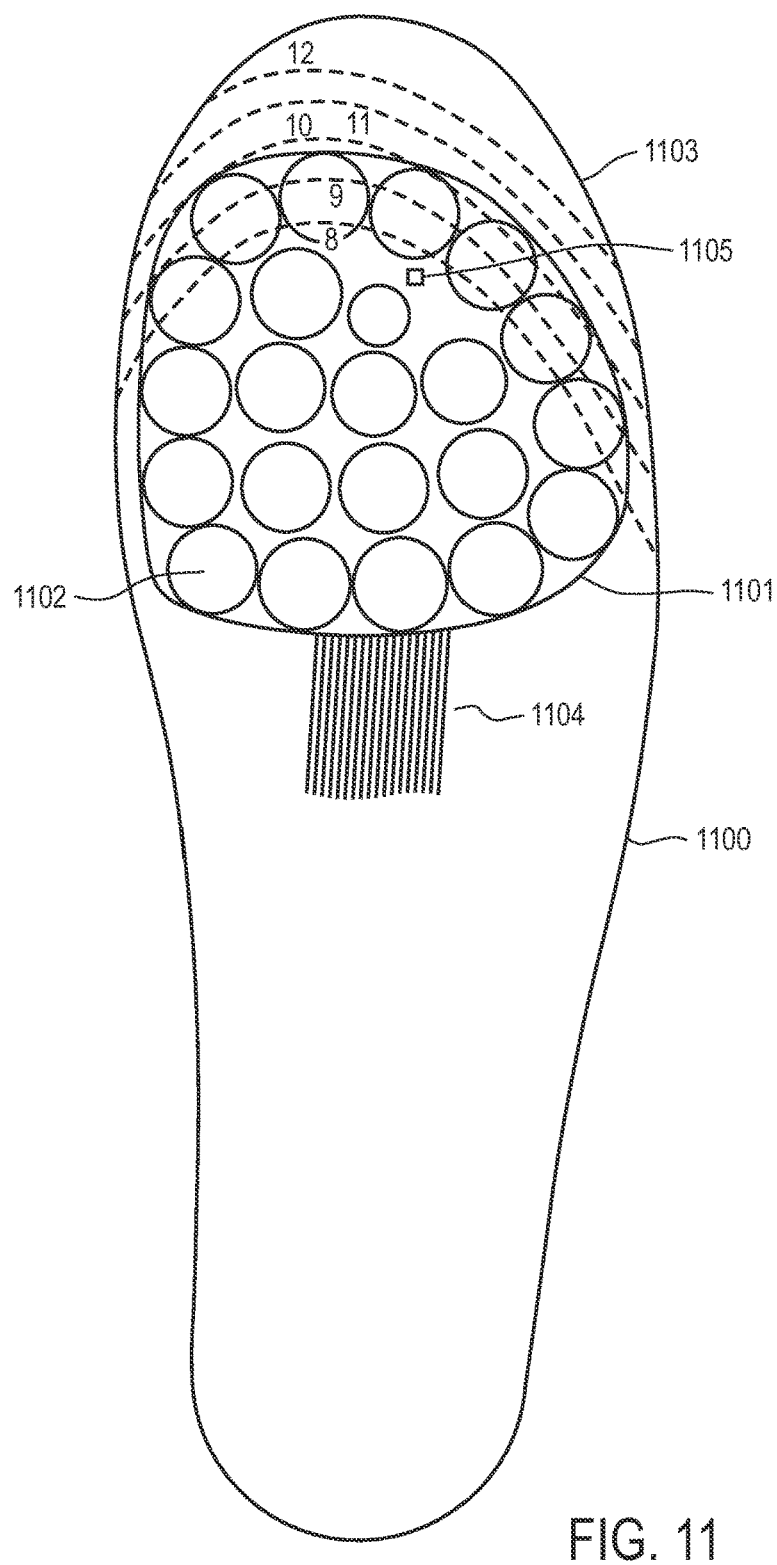
FIG. 11 illustrates an insert configured in accordance with an embodiment of the invention.

One embodiment includes two TPIs (Thin Platform Inserts). Each TPI has its own functional role. The TPIs can be attached together to form the insert with a thickness of less than 3 mm, or more particularly less than 2 mm, and standard shoes/insole sizes for males and females. A universal TPI (U-TPI) is creatively designed to be cut to fit any size for all genders. As shown in FIG. 11, where 1100 is the TPI, 1101 is the force sensors areas, 1102 is one of the force sensors, 1103 is one of the cutting lines for a specific size, 1104 are the electrical line and traces made in the middle of the TPI, 1105 is the location of the IMU chip. The user may end up cutting into some of the force sensors 1102 in the sensors area 1101. In this case the user will indicate in the mobile application the size he/she is using after the cut, and also the firmware will be able to sense automatically that certain force sensors corresponding to certain cut sizes have ceased to work and will not scan those sensors anymore.

An additional method is to custom design the TPI into a shoe or insole for a specific person. TPI substrates can be made from Flexible PCB, PET plastics, polycarbonate, polyethylene (lightweight, stiff, but prone to cracks), polyurethane or polypropylene (light weight, high stiffness, but prone to cracking). The main substrate is further protected from water by means of water proofing nano-technology or similar technologies. Additional protection layers on the top and bottom of the TPI are made either from leather, ethylene vinyl acetate (EVA) (soft, firm, shock absorbent, tear resistant, rigid, but has limited cushioning), carbon fiber composite (thin, ultralight, rigid, very durable, but tough to cut, and more expensive), acrylic (tough, but prone to cracking), or a thin layer of polyethylene foam (durable, lightweight, resilient to compression, has limited shock absorption).

In another embodiment the TPI can be designed to not only measure the forces that are pushing downwards towards the pedal from 0 o'clock to 6 o'clock, but also be able to measure forces when pulling up on the shoe from 6 o'clock to 12 o'clock/0 o'clock. This is done by what is called the TPI-wings (TPI-w), this also can be U-TPI-w. U-TPI-w or TPI-w can be an independent device or it can be a device embedded and designed in the shoe.

Figure 12:
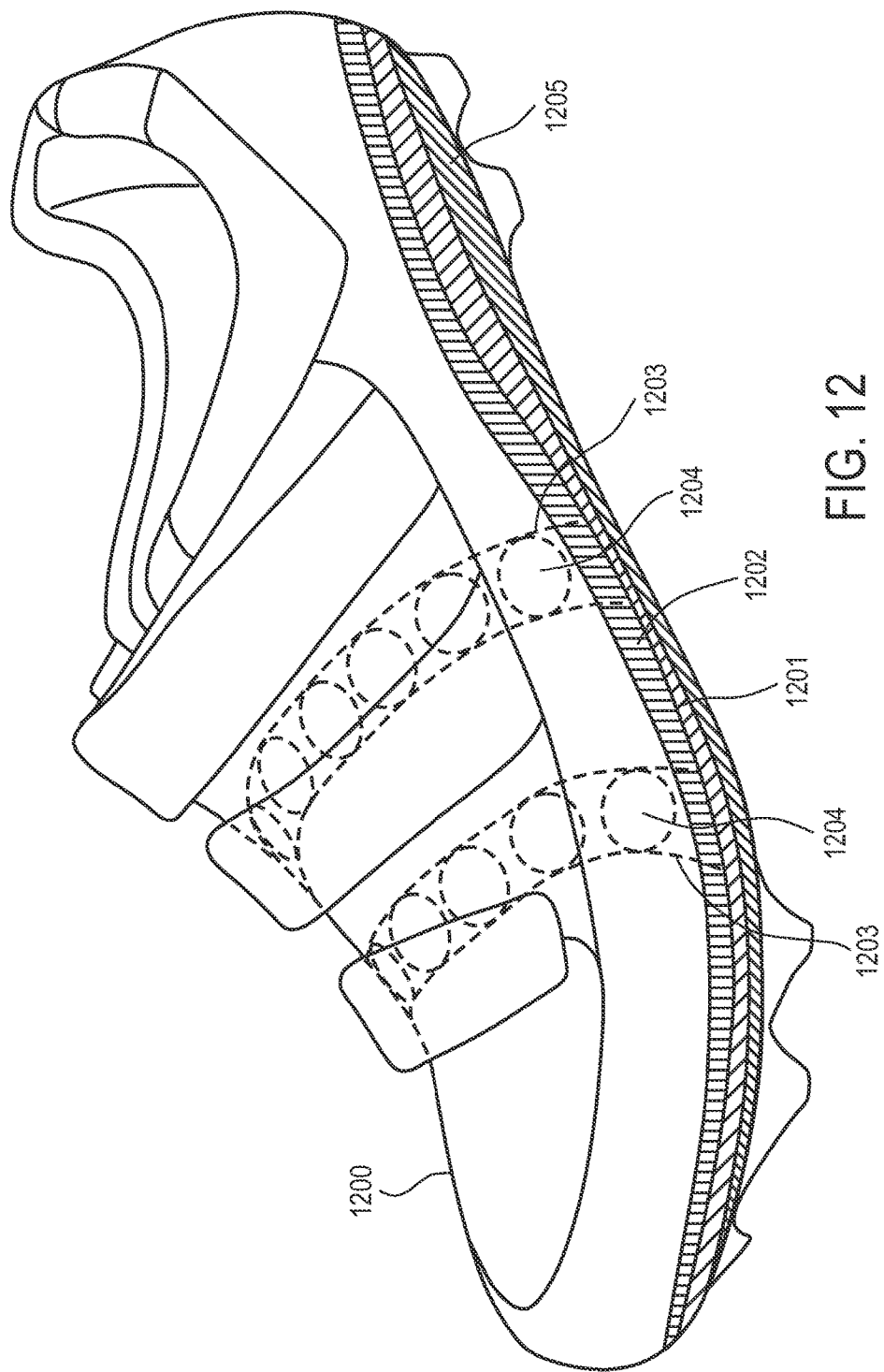
FIG. 12 illustrates a shoe incorporating circuitry associated with an embodiment of the invention.

FIG. 12 illustrates a cycling shoe 1200. 1205 is the lowest padding area in the shoe, above it is 1201 which is the U-TPI-w, above that is the original insole 1202 or the user custom made insole. 1203 are the wings of the TPI, each wing has force sensors represented as 1204. A U-TPI-w can have more than two wings. In this design the wings are capable of measuring not only the pull-up forces exerted by the cyclist or any sports person but also the side impact of the foot on the side of the shoe. The pull-up forces represent the amount of power the cyclist exerts during 6 o'clock to 0 o'clock, which are then added to the total power the cyclists had done through the whole revolution starting with the push down and the pull-up. The side impact forces are important to understand since these forces are contributing to unaligned foot inside the shoes and also for loss in power especially when comprehensively the firmware looks at all the data from the IMU, push force sensors profile and other data. This U-TPI-w can also be fitted and designed into socks. Also in another embodiment the U-TPI-w can have another wing by the arch area to gather most of the electronics needed for the device, this is due to the fact the that the arch area in the shoe has the least push forces from weight and general pushing on the shoe, this area is the most protective area for most of the electronics. In another embodiment, the shoe can have an air inlet and vent in the sole where air enters and some of the air is kept in a compartment where it is accumulated until it is vented through a small rotating device with a coil that generates electrical energy. Hence, with every step or cycling revolution the energy harvesting occurs to feed more electrical energy back into the battery.

The following is a discussion of TPI-0 force and orientation TPI sensors, processor and electronic devices. In one embodiment an ARM cortex processor and its supporting electronics are utilized. The processor is the main computing element residing inside the TPI sensor. It is responsible to read all the sensors on each TPI. It can be operating on high sampling rate for better accuracy specifically for cyclists and sprint runners as an example. Once it collects readings from the sensors, it applies signal processing and/or machine learning algorithms to extract information about the location of force points, the amount of force, also converting raw orientation information into Automatic heading information (AHRS) using accelerometer, gyrometer, or magnetometer. This processor can also manage the charging circuitry of the battery through direct connection or through wireless coil. It can also manage energy harvesting circuitry and drive it directly to the processor to wake up or to recharge the battery. The processor is also responsible for Dynamic Processing Locale (DPL).

This processor can also perform diagnostics on the TPI device during offline hours and online use by the user to make sure all components are working properly. The software architecture can be portable across the embedded processor, smart phones, tablets or other computing devices. Hence, in any case, where the processor is overloaded and cannot perform full computing mode, it can automatically notify the processor on the phone or tablet to offload some of the processing and computing needs by cross negotiating the processing load (as referenced earlier with the acronym DPL). In the case where the embedded processor is offloading to the phone processor, the embedded processor will only pass the raw sensing information from the sensors and let the TPI phone application do all the machine learning and signal processing before displaying. This load negotiation can also be used between the phone application and a cloud processing system/application. This has the advantage of load balancing battery usage among the TPI, the phone, and the Cloud. This can be done by doing dynamic shifting of the software functional module in real time—for example TPI negotiate and request from the phone to take over for example processing of the IMU or the force sensors, or other sensing elements or other computational functionalities. In case there is no phone carried with the user, and this can be determined automatically by BLE negotiation phase, the TPI processor can save all the data on a flash memory to be retrieved later by the phone, PC, or the cloud using wire or wireless (WIFI, BLE, or other) for additional computing or for displaying only. In the case of the TPI processor running in full computing mode, the processor can compute all the information from the sensors and correlate these data across the needed sensors for a specific timeline. As an example, for runners the TPI processor can be able to correlate two sensors, the force sensors and IMU at the time the foot lands (on the heel or other areas) the processor can know how much g-force the landing produced by reading IMU data. The processor can know the location of the landing by checking which force sensor was active when the landing of the foot happened. The processor can also know the roll, pitch, yaw (AHRS) orientation of the foot was at landing time from the sensor groups and the IMU data. Also this data can be correlated to the muscle exertion taking place in the bottom muscles of the foot at specific times of landing or lifting off the foot which is measured from the force sensors and IMU (hence three sensor correlation). TPI and socks can also work together to correlate the data between hydration cycle and the gait line condition of the runner during hydration, before and after, and correlate it with the muscles activities across the foot and the legs. In the case of two IMUs and its supporting circuitry—each is 9 Degree of Freedom (DOF) capable. In another embodiment, 16 force sensors or matrix of high resolution multi touch sensors (>800 microsensors) are used. OP-AMPs produce linear output from the force sensors. Two way 16 to 128 port multiplexer for discrete or matrix sensors may be used. EEPROM/Flash memory is used to data log for example an equivalent of 200,000 steps (when no phone is present) or >8 hrs of continuous cycling. Vibration elements may be used for notifications and massage. Various protocols may be used, such as ANT+ and LE-Bluetooth (BLE). In one embodiment, a sampling rate >5000/sec per one sensor is used.

Power may be processed as follows. A coil may be used for wireless charging. 16 to 64 piezoelectric matrix sensors may be used for energy harvesting. Energy harvesting circuitry may be utilized. Lithium ion polymer or other solid state rechargeable battery may be used. A coin battery may be used in certain embodiments. The device may incorporate GPS circuitry. Continuous wireless charging may be used as the user is cycling or doing other activities.

One embodiment of a sock implementation may include EMG sensing for muscle activities and lactic acid build up measurements, sweat rate/hydration sensing, heart rate sensing, and ankle orientation sensing. Micro ultrasonic sensors may also be used.

One embodiment incorporates the following into pants: EMG sensing, orientation sensing, hydration and solar renewable energy.

Those skilled in the art will recognize many advantages associated with embodiments of the invention. First, there is the ability to aggregate all the data from all sensors in all devices in real time and make critical decisions based on current real time real time voice coach notifications, personal data, historical personal data, and community data to identify effectiveness of the workout or potential injuries. The type of data detected is gait, force profile of each foot, foot orientation in 9 degrees, muscles activities and exertion in the bottom of the foot and ankle, hydration levels, temperature, humidity, heart rate, touch time, strike area, power for runners, pronation, supination, heart rate variation, muscles activities and exertion in muscles below the knee and above the knee, position and angular position and angular speed of hip. This data can be aggregated and processed on the TPI-0 processor and other processors in socks or pants or remote computing device(s) and be displayed to the user.

TPI for use in cycling is capable of measuring cadence, power, several derivative of power parameters, pronation, supination, knee exposers to potential stresses or wrong movements, angular velocity and injury predictions. Many parameters like power, foot force profile, g-forces and more are measured real time with high sampling rates during each revolution of cycling from top location of the pedal to bottom, and back to top for both feet at the same time.

Software algorithms can apply machine learning and signal processing to aggregate the specific sensors above and specific locations of the sensors to display and predict specific information. These same algorithms, predictive analytics, and/or comparative analytics software can also run in the cloud for more detailed current and historical data.

This device can sense the exact foot position inside the shoes (in comparison to other devices which measure bare foot on a mat or foot in shoes on a mat, or a restricted insole touching the foot). The device affords the option to use any insole, any shoes, and floor type. The device does not require the user to be inside a room in a clinic, or exercise room but rather the device can collect real data of real life scenarios and real time stream to cloud for coaches which help identify issues with the effectiveness of the activities which most of the time does not exhibit itself in restricted and limited clinics or rooms.

Advantageously, there is battery power and load balancing among the TPI device, the remote computing device (e.g., phone), and the Cloud. This can avoid the TPI device, the sock, the pant or the remote computing device (e.g., phone/tablet) from running out of power battery. The device can be used to compare different shoes for different activities, and also compare shoes when trying different ones at time of purchase. In shoe comparison mode, the device can list all the difference in all the TPI parameters.

The device has the ability to predict the lifetime of the shoes through max number of the steps (max 200,000) or maximum number of revolutions for cycling, and by measuring the comparative g-forces on the shoe, comparative gait and comparative force analysis.

The device can have a matrix of interleaved force sensors, solid state strain gauges, barometric pressure/force sensors, solid state strain gauges, and heated elements—which provide both force profile of the foot and keep the foot warm in cold weather. The matrix can have electronic data buffers to collect data temporarily of all horizontal and vertical readings, and hence improve sampling rate and processor performance.

The device has the ability to authenticate a person by using a matrix of micro-ultrasonic device situated under the big toe to read the toe-finger-print. The device may also be configured to read real time EMG signal from muscles surrounding the Plantar Fasciitis tissue. The device also has the ability to read real time EMG signal of muscles surrounding the ankle and Achilles. Further, the device has the ability to read real time EMG signal of muscles below and above the knee and the orientation of these areas. The device may be configured to measure real time the orientation of the foot, force profile, and gait line.

The device may aggregate data from sensors around the foot, ankle, and leg to identify certain thresholds and limits to potentially identity risk of injuries. Real time coaching is possible through headphone or a small accompanied device to wear on the wrist or ear. Real-time sharing of all aggregated data is possible through a simple intuitive interface using the mobile phone and/or internet to the cloud account of user's real coach, doctor, colleague, family or others. There is an ability to replay animation of any exercise and activity the user did in the past, this 3D animation is based on all the data that has been saved on the remote computing device or cloud. This can enable the user to compare visually the improvements or regression in activities. Advantageously, the device has the ability to harvest electrical energy from the act of the force exerted on the TPI and the foot, and drive that into charging a battery for the device. The device also has the ability to identify in real time the corresponding relationship between the two feet in regard to force loads, center of gravity and mass, relative orientation, touch time, forward speed, angular speed, in the air orientation, power, gait lines and all other biomechanics data. The device can also identify the relative orientation and angles and orientation of both ankles, legs, knees, and hip for forward speed, vertical oscillations, angular speed, power, cadence . . . etc.

In some embodiments there is the ability to run the low end version of the device without a processor and instead pass all the raw information to the phone and the cloud to be processed and displayed. The device is capable of accurate measurements of force profile and gait line analysis, for example with less than 1% error. The device has no on/off switch for best user experience. Rather the device can come on instantaneously and automatically by sensing force and movement of the foot which causes the system to come out of sleep mode and to enter active mode. The device is applicable to a variety of personas and use cases.

The device has the ability to massage the foot using the vibration elements after an activity based on the most force points exerted. Data can be encrypted from device processor to the phone and to the cloud. There is an ability to synchronize foot and legs activity with a video camera in a confined place or with a mini quad-copter flying in front of the user in active mode.

Personas and applications that may successfully utilize the device include hardcore runners, track and field athletes (sprinters, jumpers and hurdlers), cyclists (Road, Mountain, BMX, Indoor spinning, Track), joggers, walkers, hikers, distance runners, trial runners, team coaches and managers, surgeons, warehouse personnel, dancers of all type of dances, skiers, ice skaters, gamers, diabetes patients, gait patients, potential-for-falling for seniors, gait authentication, robotics and animation mirroring, motion capture development injury avoidance, walking, skiing and other activities for the blind, women high heel impact analysis on the foot, posture when standing and while active, military, firefighters, police personal in action needing to know and be alerted if any of their comrades fell and is not moving, shoe comparisons and decision when you plan to visit the shoe store and buy a shoe, shoe lifetime analysis and profile.

While this specification contains many specifics, these should not be construed as limitations on the scope of the disclosure or of what may be claimed, but rather as descriptions of features specific to particular embodiment of the disclosure.

Certain features that are described in the context of separate embodiments can also be implemented in combination. Conversely, various features that are described in the context of a single embodiment can also be implemented in multiple embodiments separately or in any suitable subcombination. Moreover, although features may be described above as acting in certain combinations, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Embodiments of the invention can, for example, be implemented by software, hardware, or a combination of hardware and software. Embodiments of the invention can also be embodied as computer readable code on a computer readable medium. The computer readable medium is any data storage device that can store data which can thereafter be read by a computer system. Examples of the computer readable medium generally include read-only memory and random-access memory. More specific examples of computer readable medium are tangible and include Flash memory, EEPROM memory, memory card, CD-ROM, DVD, hard drive, magnetic tape, and optical data storage device. The computer readable medium can also be distributed over network-coupled computer systems so that the computer readable code is stored and executed in a distributed fashion.

The many features and advantages of the present invention are apparent from the written description. Further, since numerous modifications and changes will readily occur to those skilled in the art, the invention should not be limited to the exact construction and operation as illustrated and described. Hence, all suitable modifications and equivalents may be resorted to as falling within the scope of the invention.

The invention claimed is:

1. An in-shoe monitoring system, comprising:
a shoe insert including at least:
a flexible substrate;
a plurality of force sensors secured to the flexible substrate;
at least one position sensor;
at least one motion sensor;
a microcontroller secured to the flexible substrate and operational to receive sensor data from the plurality of force sensors, the at least one position sensor, and the at least one motion sensor; and
a wireless transceiver operational to at least transmit sensor data from the plurality of force sensors, the at least one position sensor, and/or the at least one motion sensor; and
a portable computing device operational to receive the sensor data from the wireless transceiver;
wherein the sensor data is associated with a user's foot within a shoe having the shoe insert, and wherein the portable computing device is further operational to process the sensor data to determine shoe consumption data characterizing shoe usage or shoe lifetime analysis.

2. The in-shoe monitoring system as recited in claim 1, wherein the portable computing device is further operational to process the sensor data to determine foot usage data.

3. The in-shoe monitoring system as recited in claim 2, wherein the foot usage data is associated with a user's foot within a shoe having the shoe insert.

4. The in-shoe monitoring system as recited in claim 2, wherein the foot usage data includes one or more of foot landing data, foot orientation data, gaitline, or force profile.

5. The in-shoe monitoring system as recited in claim 1 wherein the shoe insert includes a piezo-resistive device.

6. The in-shoe monitoring system as recited in claim 1 wherein the portable computing device computes a force value.

7. The in-shoe monitoring system as recited in claim 1 wherein the microcontroller performs calibration.

8. The in-shoe monitoring system as recited in claim 1 wherein the shoe insert includes a film of fireproof material.

9. The in-shoe monitoring system as recited in claim 1 wherein the portable computing device computes pull-up force.

10. The in-shoe monitoring system as recited in claim 1 wherein the portable computing device negotiates a dynamic processing protocol.

11. The in-shoe monitoring system as recited in claim 1 wherein the shoe insert is less than 2 mm.

12. The in-shoe monitoring system as recited in claim 1 wherein the shoe insert includes a gyrometer.

13. The in-shoe monitoring system as recited in claim 1 further comprising a matrix of piezoelectric sensors for energy harvesting.

14. The in-shoe monitoring system as recited in claim 1 further comprising a solid state rechargeable battery.

15. The in-shoe monitoring system as recited in claim 14 wherein the solid state rechargeable battery is wirelessly recharged.

16. The in-shoe monitoring system as recited in claim wherein the plurality of force sensors include a matrix of interleaved force sensors.

17. The in-shoe monitoring system as recited in claim wherein the plurality of force sensors include a matrix of solid state strain gauges.

18. The in-shoe monitoring system as recited in claim 17 further comprising a matrix of barometric pressure sensors.

19. The in-shoe monitoring system as recited in claim 17 further comprising heating elements.

* * * * *